United States Patent
Miyata

(10) Patent No.: US 9,240,557 B2
(45) Date of Patent: Jan. 19, 2016

(54) AMINE DERIVATIVE, ORGANIC ELECTROLUMINESCENCE MATERIAL, AND ORGANIC ELECTROLUMINESCENCE DEVICE INCLUDING THE SAME

(71) Applicant: SAMSUNG DISPLAY CO., LTD., Yongin, Gyeonggi-Do (KR)

(72) Inventor: Yasuo Miyata, Yongin (KR)

(73) Assignee: SAMSUNG DISPLAY CO., LTD., Yongin, Gyeonggi-Do (KR)

(*) Notice: Subject to any disclaimer, the term of this patent is extended or adjusted under 35 U.S.C. 154(b) by 142 days.

(21) Appl. No.: 14/091,549

(22) Filed: Nov. 27, 2013

(65) Prior Publication Data

US 2014/0151661 A1 Jun. 5, 2014

(30) Foreign Application Priority Data

Nov. 30, 2012 (JP) .................. 2012-263867

(51) Int. Cl.
| | |
|---|---|
| *C07D 235/02* | (2006.01) |
| *C07D 403/12* | (2006.01) |
| *C07D 405/14* | (2006.01) |
| *C07D 405/12* | (2006.01) |
| *C07D 409/12* | (2006.01) |
| *C07D 409/14* | (2006.01) |
| *H01L 51/00* | (2006.01) |
| *H01L 51/50* | (2006.01) |

(52) U.S. Cl.
CPC .......... *H01L 51/0072* (2013.01); *C07D 235/02* (2013.01); *C07D 403/12* (2013.01); *C07D 405/12* (2013.01); *C07D 405/14* (2013.01); *C07D 409/12* (2013.01); *C07D 409/14* (2013.01); *H01L 51/0061* (2013.01); *H01L 51/0073* (2013.01); *H01L 51/0074* (2013.01); *H01L 51/5056* (2013.01); *H01L 2251/308* (2013.01)

(58) Field of Classification Search
None
See application file for complete search history.

(56) References Cited

U.S. PATENT DOCUMENTS

2007/0231503 A1   10/2007   Hwang et al.

FOREIGN PATENT DOCUMENTS

| CN | 102190627 A | 9/2011 |
| JP | 2007-534814 A | 11/2007 |
| JP | 2009-526111 A | 7/2009 |
| JP | 2010-528070 A | 8/2010 |
| WO | WO 2007090773 A1 * | 8/2007 |
| WO | WO 2010/110553 A2 | 9/2010 |
| WO | WO 2012/091471 A2 | 7/2012 |

OTHER PUBLICATIONS

CN102190627 (Sep. 21, 2011) [machine translation of the Description].*

* cited by examiner

*Primary Examiner* — Michael Barker
(74) *Attorney, Agent, or Firm* — Lee & Morse, P.C.

(57) ABSTRACT

An amine derivative having a phenanthroimidazole group, an organic electroluminescence material, and an electroluminescence device, the amine derivative being represented by Formula 1, below:

[Formula 1]

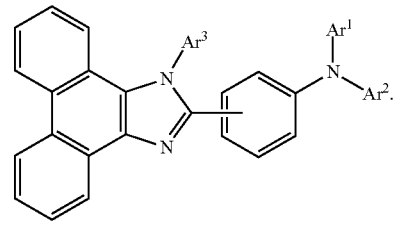

12 Claims, 1 Drawing Sheet

AMINE DERIVATIVE, ORGANIC ELECTROLUMINESCENCE MATERIAL, AND ORGANIC ELECTROLUMINESCENCE DEVICE INCLUDING THE SAME

CROSS-REFERENCE TO RELATED APPLICATION

Japanese Patent Application No. 2012-263867, filed on Nov. 30, 2012, in the Japanese Patent Office, and entitled: "AMINE DERIVATIVE, ORGANIC ELECTROLUMINESCENCE MATERIAL, AND ORGANIC ELECTROLUMINESCENCE DEVICE INCLUDING THE SAME," is incorporated by reference herein in its entirety.

BACKGROUND

1. Field

Embodiments relate to an amine derivative, an organic luminescence material, and an organic electroluminescence (EL) device including the same.

2. Description of the Related Art

In recent years, organic electroluminescence (EL) displays are one type of image displays that have been actively developed. Unlike a liquid crystal display (or the like), the organic EL display is so-called a self-luminescent display that recombines holes and electrons injected from an anode and a cathode in a light-emitting layer to thus emit light from a light-emitting material including an organic compound, thereby displaying an image.

An organic electroluminescence (EL) device may include a plurality of layers having different characteristics, e.g., a light-emitting layer, a layer transporting carriers (e.g., holes or electrons) into the light-emitting layer, or the like.

SUMMARY

Embodiments are directed to an amine derivative, an organic luminescence material, and an organic electroluminescence (EL) device including the same.

The embodiments may be realized by providing an amine derivative having a phenanthroimidazole group, the amine derivative being represented by Formula 1, below:

[Formula 1]

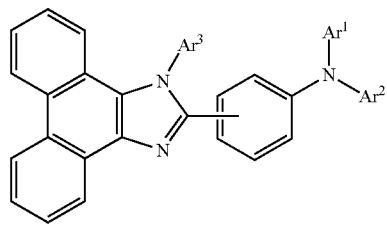

wherein $Ar^1$, $Ar^2$, and $Ar^3$ are each independently one of a substituent aryl group or a substituent heteroaryl group, and at least one of $Ar^1$, $Ar^2$, or $Ar^3$ has at least 12 carbon atoms.

The amine derivative having the phenanthroimidazole group may be represented by Formula 2, below:

[Formula 2]

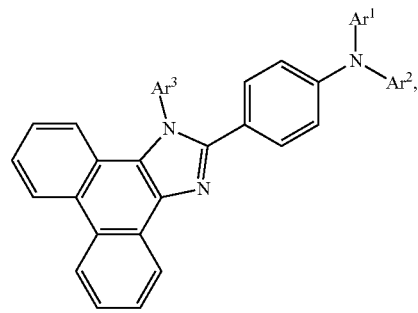

wherein $Ar^1$, $Ar^2$, and $Ar^3$ may be as defined with respect to Formula 1.

$Ar^1$, $Ar^2$, and $Ar^3$ may be different substituents from one another.

$Ar^1$, $Ar^2$, and $Ar^3$ may each independently be one of a substituent dibenzoheterole group or a substituent aryl group having 6 to 18 carbon atoms.

$Ar^1$, $Ar^2$, and $Ar^3$ may each independently be one of a substituent dibenzofuran, a substituent dibenzothiophene, a substituent carbazole, a substituent fluorene, or a substituent phenyl.

The embodiments may also be realized by providing an organic electroluminescence material including an amine derivative having a phenanthroimidazole group according to an embodiment.

The embodiments may also be realized by providing an electroluminescence device including an anode; a cathode; and a light-emitting layer and a hole transport layer between the cathode and the anode, wherein the hole transport layer includes an amine derivative having the phenanthroimidazole group according to an embodiment.

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
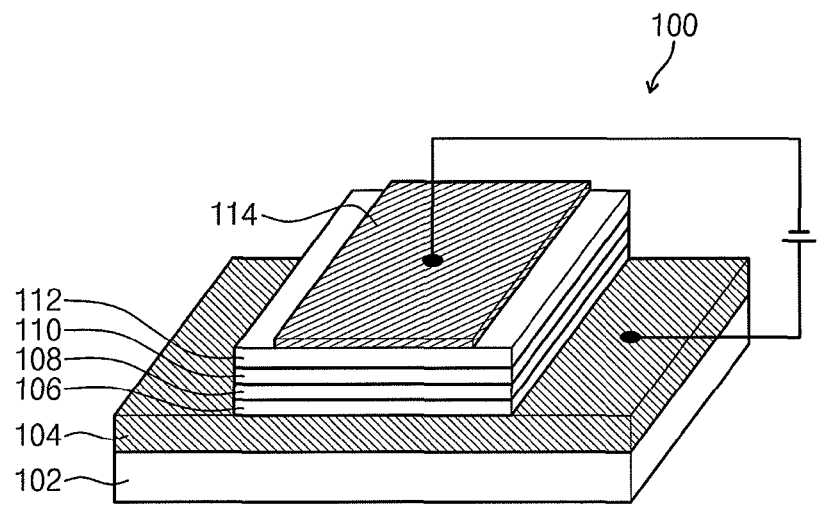
FIG. 1 illustrates a schematic perspective view of a structure of an organic EL device according to an embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. Like reference numerals refer to like elements throughout.

An organic EL material according to an embodiment may include an amine derivative having a phenanthroimidazole group. For example, the amine derivative having a phenanthroimidazole group may be represented by Formula 1, below.

[Formula 1]

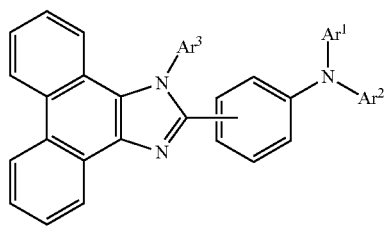

In Formula 1, Ar¹, Ar², and Ar³ may each independently be one of a substituent aryl group or a substituent heteroaryl group. At least one of Ar¹, Ar², and Ar³ may have at least 12 carbon atoms.

In "the substituent aryl group" or "the substituent heteroaryl group" of Ar¹, Ar², and Ar³, the aryl group and the heteroaryl group may include, e.g., a phenyl group, a naphthyl group, an anthracenyl group, a phenanthryl group, a biphenyl group, a terphenyl group, a fluorenyl group, a triphenylene group, a biphenylene group, a pyrenyl group, a benzothiazolyl group, a thiophenyl group, a thienothiophenyl group, a thienothienothiophenyl group, a benzothiophenyl group, a dibenzothiophenyl group, a dibenzofuryl group, an N-arylcarbazolyl group, an N-heteroarylcarbazolyl group, an N-alkylcarbazolyl group, a phenoxazyl group, a phenothiazyl group, a pyridyl group, a pyrimidyl group, a triazyl group, a quinolinyl group, or a quinoxaryl group. In an implementation, the aryl or the heteroaryl group of Ar¹, Ar², and Ar³ may include a phenyl group, a naphthyl group, a biphenyl group, a terphenyl group, a fluorenyl group, a triphenylene group, a dibenzothiophenyl group, a dibenzofuryl group, or an N-phenylcarbazolyl group, e.g., a phenyl group, a biphenyl group, a fluorenyl group, a triphenylene group, a dibenzothiophenyl group, a dibenzofuryl group, or an N-phenylcarbazolyl group.

In "the substituent aryl group" or "the substituent heteroaryl group" of Ar¹, Ar², and Ar³, the group may be substituted with, e.g., an alkyl group, an alkoxy group, an aryl group, or a heteroaryl group.

In "the substituent aryl group" or "the substituent heteroaryl group" of Ar¹, Ar², and Ar³, the alkyl group as a substituent of the substituent aryl group or substituent heteroaryl group may include, e.g., a methyl group, an ethyl group, a propyl group, an isopropyl group, a cyclopropyl group, a butyl group, an isobutyl group, a tert-butyl group, a cyclobutyl group, a pentyl group, an isopentyl group, a neopentyl group, a cyclopentyl group, a hexyl group, a cyclohexyl group, a heptyl group, a cycloheptyl group, an octyl group, a nonyl group, or a decyl group.

In "the substituent aryl group" or "the substituent heteroaryl group" of Ar¹, Ar², and Ar³, the alkoxy group as a substituent group of the substituent aryl group or substituent heteroaryl group may include, e.g., a methoxy group, an etoxy group, an n-propoxy group, an isopropoxy group, an n-butoxy group, an isobutoxy group, a t-butoxy group, an n-pentyloxy group, a neopentyloxy group, an n-hexyloxy group, an n-heptyloxy group, an n-octyloxy group, a 2-ethylhexyloxy group, a nonyloxy group, a decyloxy group, or a 3,7-dimethyloctyloxy group.

In "the substituent aryl group" or "the substituent heteroaryl group" of Ar¹, Ar², and Ar³, the aryl group and the heteroaryl group as substituents of the substituent aryl group or substituent heteroaryl group may be the same as the aryl group and the heteroaryl group of the "substituent aryl group" or the "substituent heteroaryl group".

In an implementation, the amine derivative having a phenanthroimidazole group compounds according to an embodiment may include any one of Compounds 1 to 28, below.

1

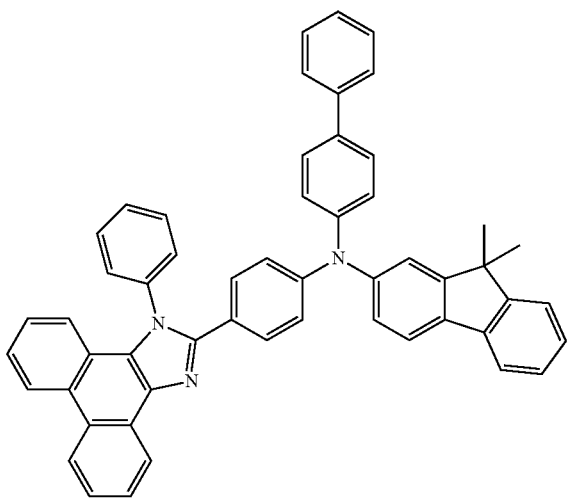

2

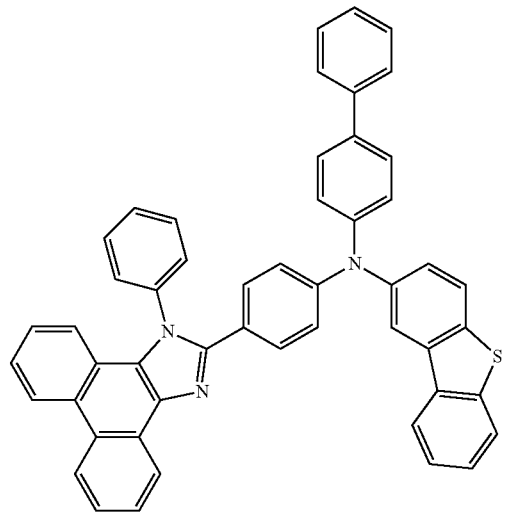

3

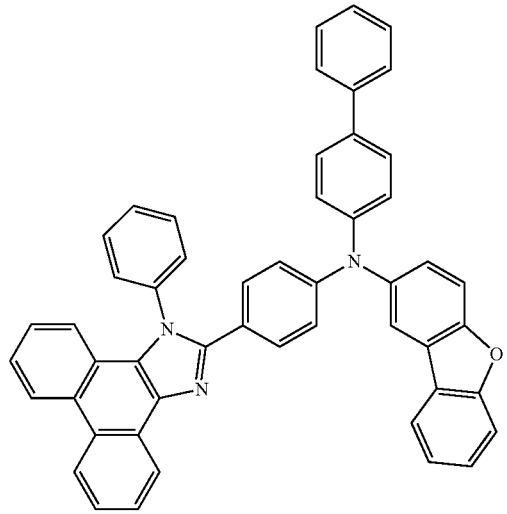

4
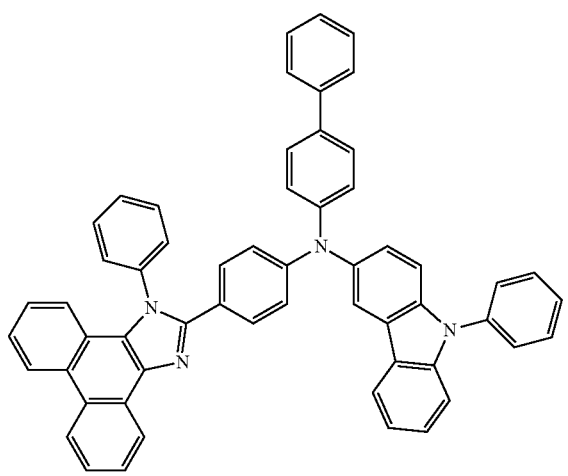
5
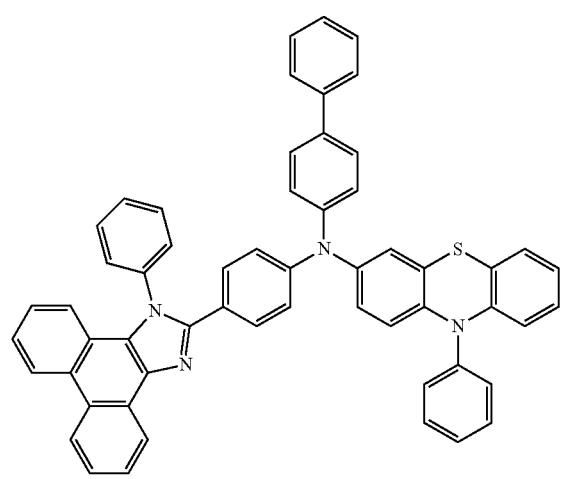
6
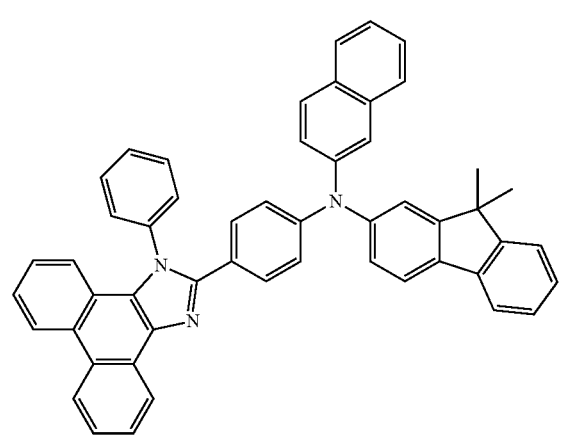
7
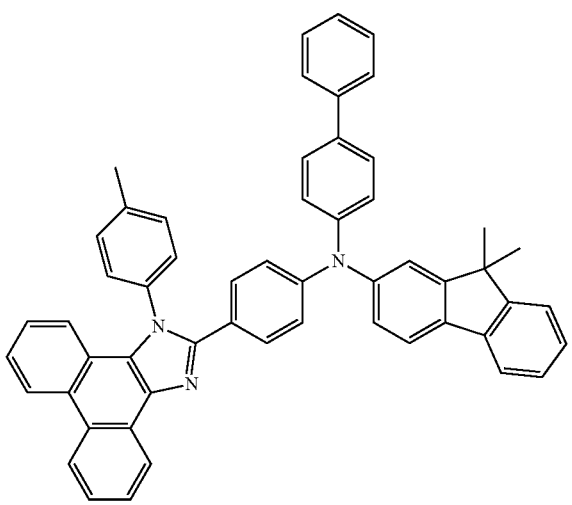
8
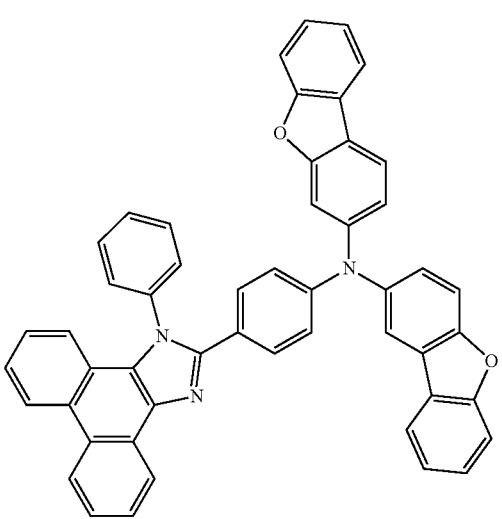
9

10
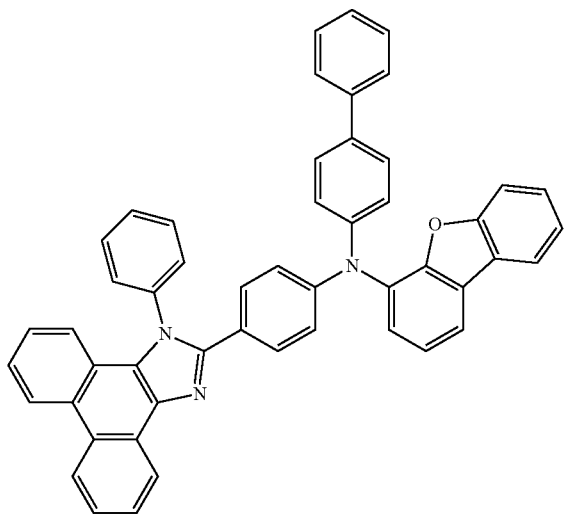
11
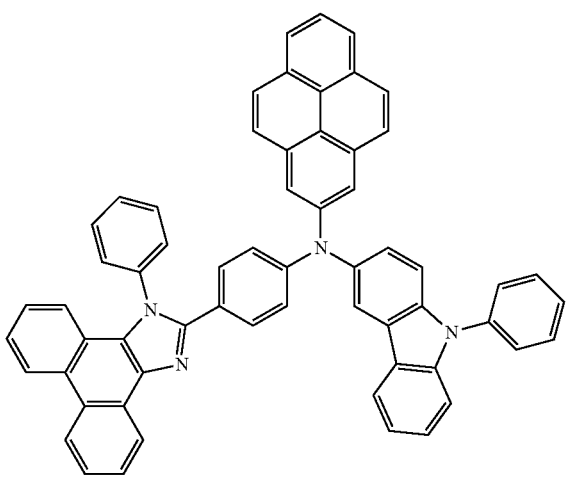
12
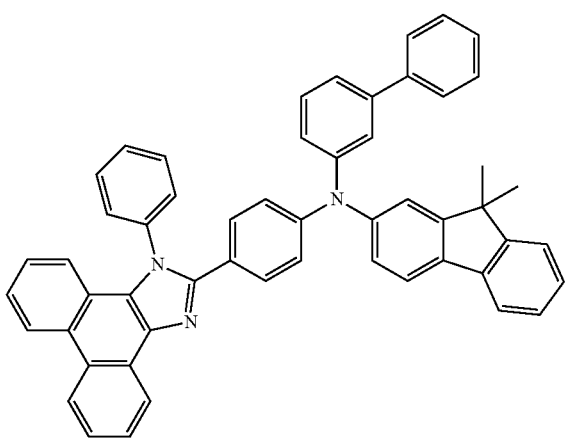
13
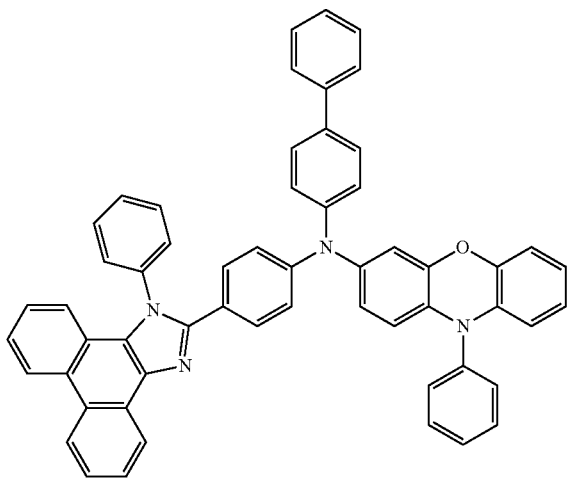
14
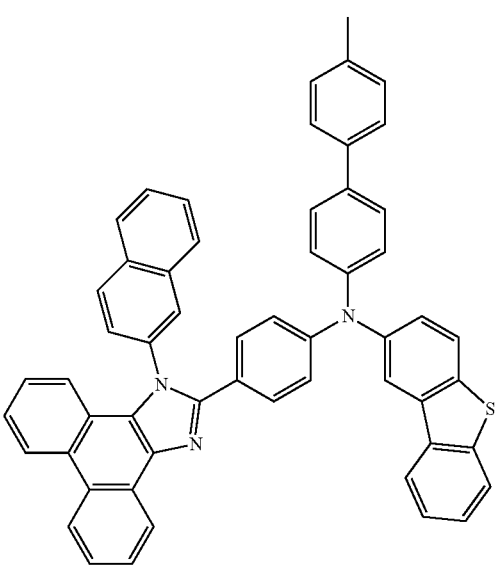
15
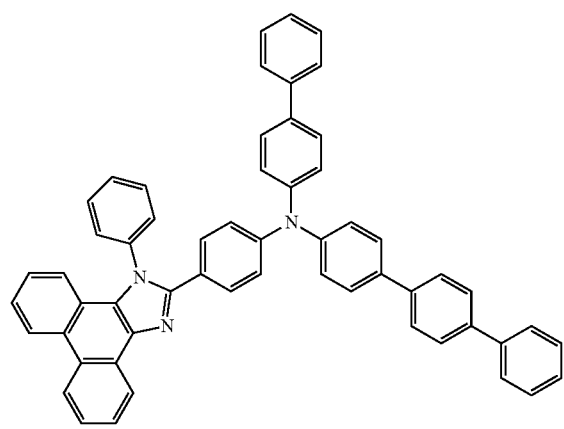

16
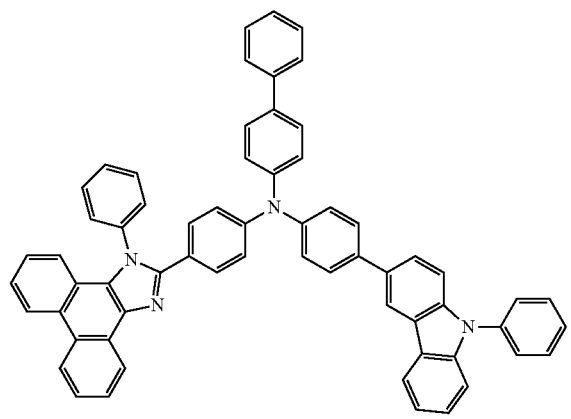
17
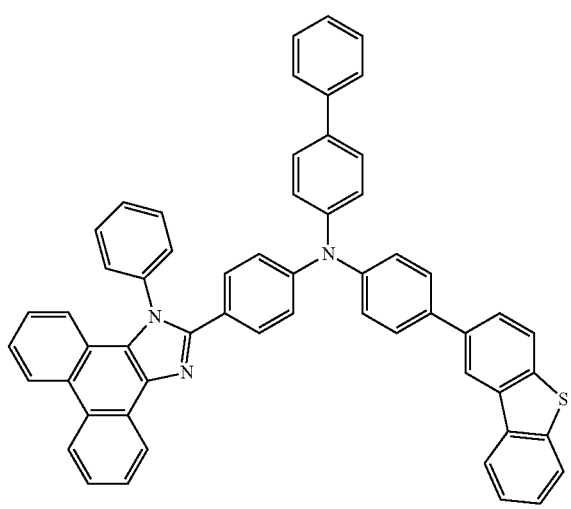
18
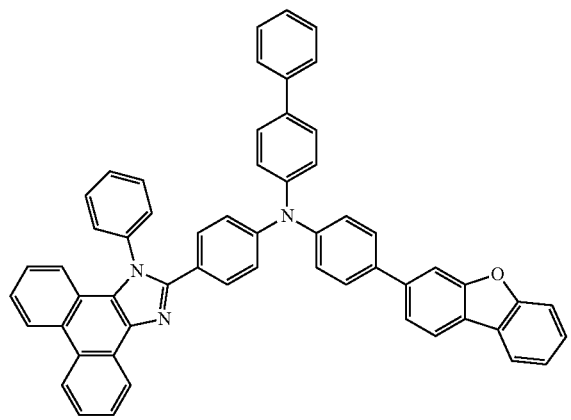
19
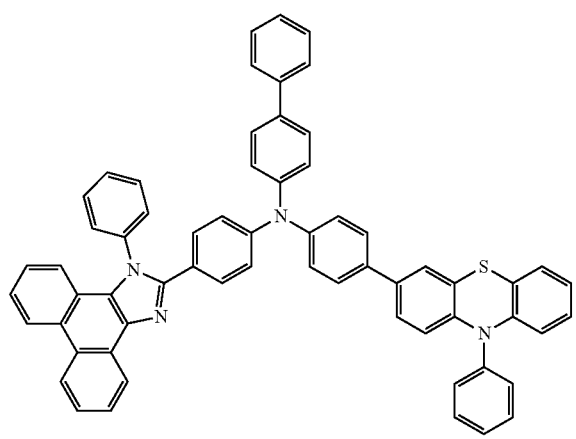
20
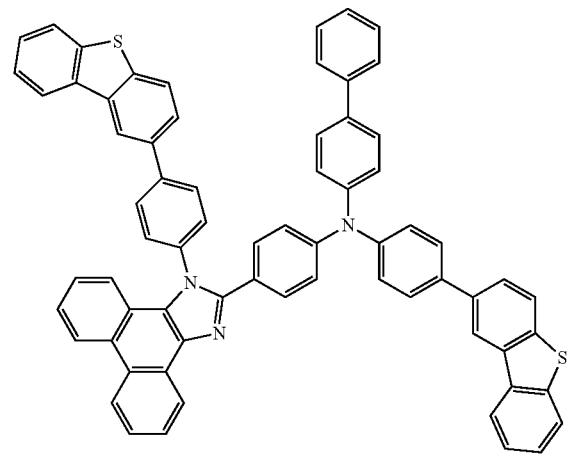

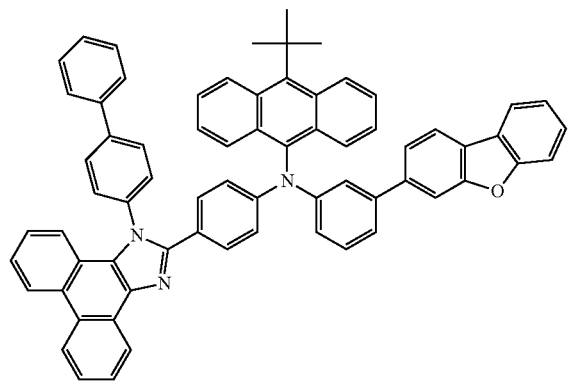
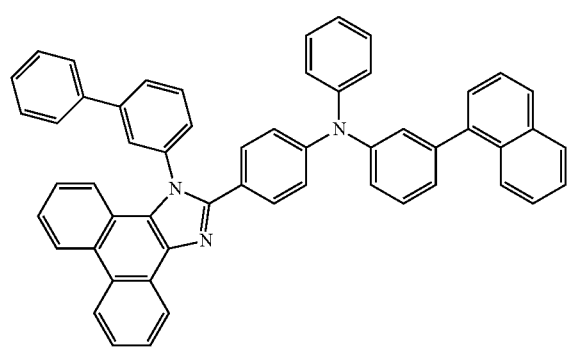
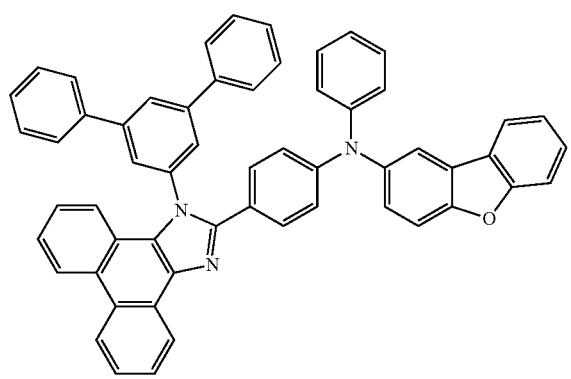
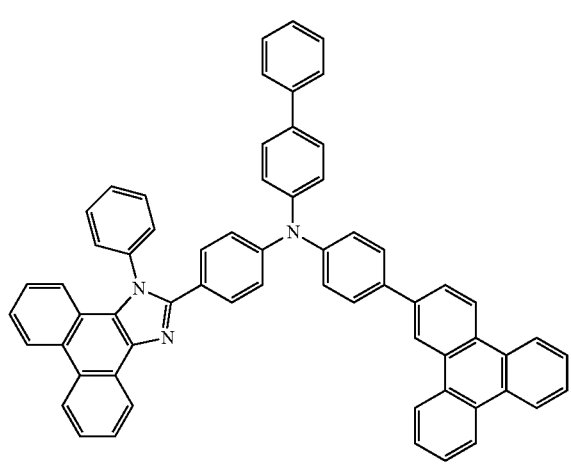
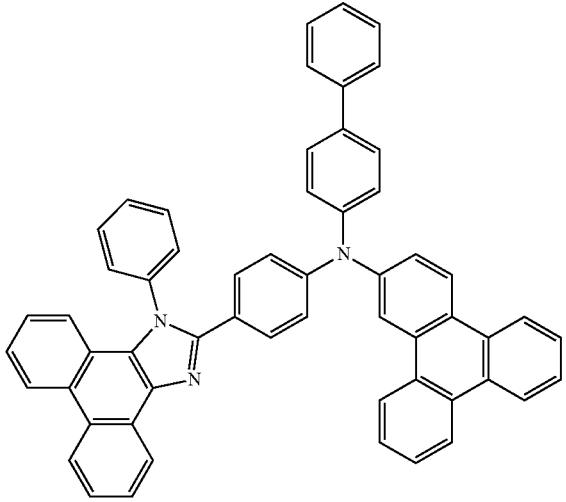
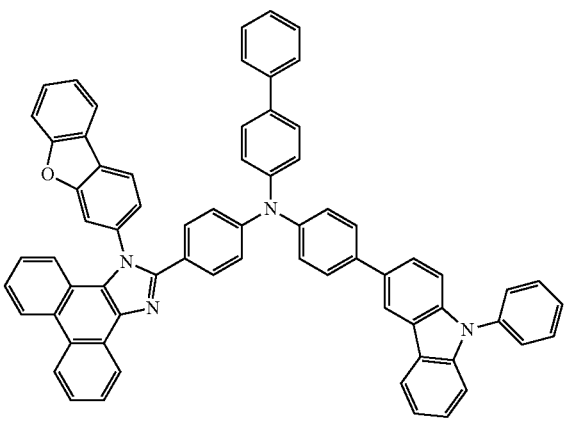
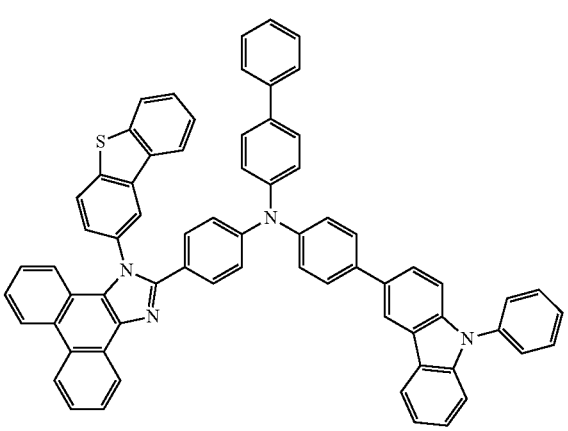
In an implementation, the amine derivative according to an embodiment may include any one of Compounds 1, 2, 3, 5, 8, 10, 11, 13, 15, 16, 17, 18, 19, 20, 25, and 26, e.g., any one of Compounds 1, 2, 3, 4, 17, 18, 25, and 26.
Organic EL Device
The amine derivative according to an embodiment may be used as a material for an organic EL device. Such an organic EL device may have, e.g., the structure illustrated in FIG. 1, but is not limited thereto.

FIG. 1 illustrates a schematic perspective view of an organic EL device 100 in which an amine derivative of an embodiment is used as a material for the organic EL device 100. Referring to FIG. 1, the organic EL device 100 may include a glass substrate 102, an anode 104 on the glass substrate 102, a hole injection layer 106 on the anode 104, a hole transport layer 108 on the hole injection layer 106, a light-emitting layer 110 on the hole transport layer 108, an electron transport layer 112 on the light-emitting layer 110, and a cathode 116 on the electron injection layer 114. In an implementation, the electron transport layer 112 may also function as an electron injection layer.

According to an embodiment, the amine derivative may be used as a material for the hole transport layer 108, and long life span of the organic EL device may be achieved.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES

A method of synthesizing an amine derivative according to an embodiment will now be described.

[Synthesis of Compound 2]

Reaction Scheme 1 shows a synthesis process of Compound 2, which is an amine derivative according to an embodiment.

[Reaction Scheme 1]

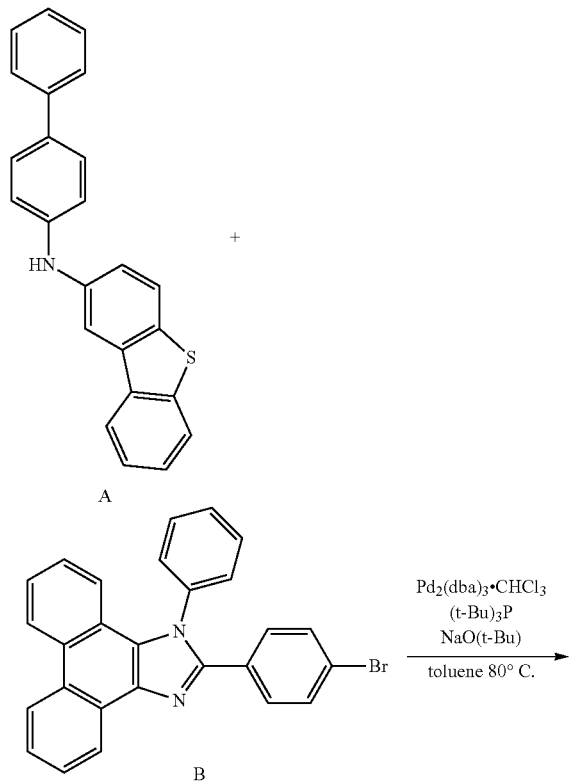

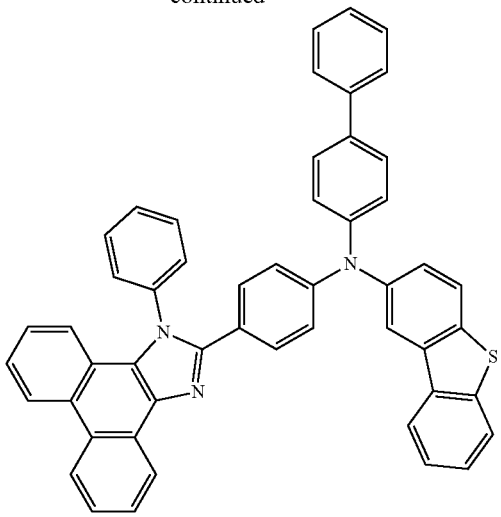

Compound 2 was synthesized as follows.

Synthesis of Compound 2

Compound A (1.58 g, 4.27 mmol), compound B (1.60 g, 3.56 mmol), Pd$_2$(dba)$_3$·CHCl$_3$ (tris(dibenzylideneacetone)dipalladium(0)-chloroform adduct) (0.37 g, 0.36 mmol), and toluene (36 mL) were introduced into a reaction container. Then, tri(t-butyl)phosphine (0.91 mL, 1.42 mmol, 1.56 M), and sodium t-butoxide (1.03, 10.7 mmol) were added, the atmosphere in the reaction container was substituted with nitrogen, and the mixture was stirred at 80° C. for 4 hours. The reaction solution was cooled, water was added to the reaction solution, and extraction was performed to obtain an organic layer. The obtained organic layer was dried by using anhydrous magnesium sulfate, was filtered, and the filtered solution was concentrated by using a rotary evaporator. The obtained crude product was purified by silica gel column chromatography (developing solvent: dichloromethane/hexane) to obtain a solid, and the obtained solid was recrystalized with a mixture of toluene and hexane to obtain a 2.25 g of targeted white powder solid (yield: 88%) (LCMS (APCI+): C$_{51}$H$_{33}$N$_3$S, measured value: 719.3083, calculated value: 719.2395).

Organic Electroluminescence Device

An organic EL device in which the above-described Compound 2 was used as a hole transport layer (and a Comparative Example) will be described.

Method of Manufacturing Organic EL Device

The organic EL device was manufactured in the following sequence by using a vacuum evaporation. A glass substrate on which an ITO layer was formed, patterned and cleaned in advance was surface-treated by using ozone. The ITO layer was 150 nm thick. After the ozone treatment, a 4,4',4"-tris(N,N-(2-naphtyl)phenylamino)triphenylamine (2-TNATA, thickness: 60 nm) layer that was a hole injection material was formed on the ITO layer.

Next, the Compounds shown in Table 1 (Compound 2 or Comparative Compound 1) as a hole transport material were formed to a thickness of about 30 nm, and a light-emitting layer in which tetra-t-butyl perylene (TPB) is doped at a ratio of 3% with respect to 9,10-di(2-naphtyl)anthracene (β-ADN) was formed to a thickness of about 25 nm by a co-evaporation.

Figure 2:
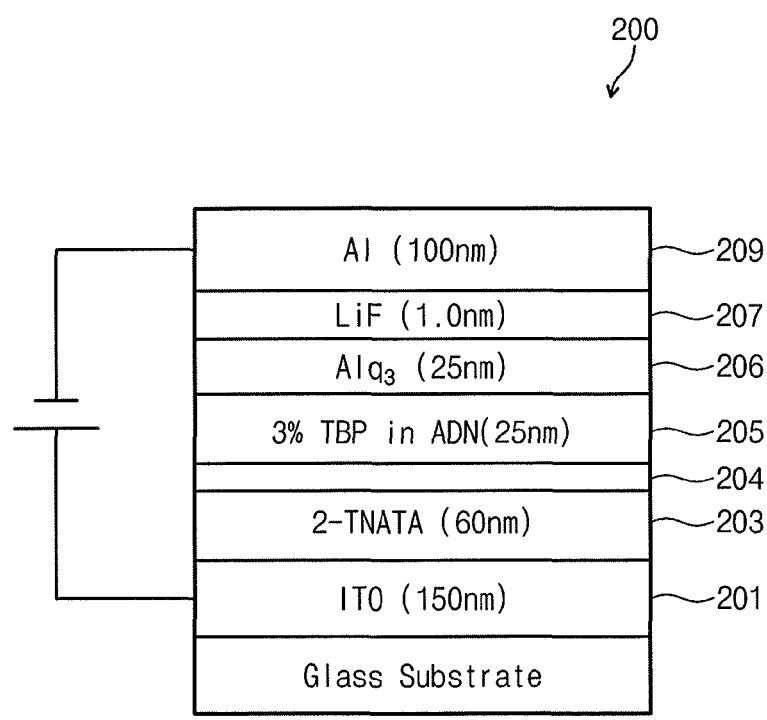
FIG. 2 illustrates a schematic view of an organic EL device manufactured using an organic luminescence material according to an embodiment.

Thereafter, an electron transport layer was formed of tris (8-quinolinolato) aluminum ($Alq_3$) to a thickness of about 25 nm, an electron injection layer was formed of lithium fluoride (LiF) to a thickness of about 1.0 nm, and a cathode was formed of aluminum to a thickness of about 100 nm to manufacture an organic EL device 200 (see FIG. 2).

The structure of Comparative Compound 1, used as a hole transport layer of an organic EL device of Comparative Example 1, is shown below. Comparative Compound 1 is different from the amine derivative according to an embodiment. For example, Comparative Compound 1 does not have a phenanthroimidazole group. Experiments that are the same as the experiments that were preformed with respect to the Compound 2 used in Example 1, except that Comparative Compound 1 was used instead of Compound 2, were performed.

(Comparative Compound 1)

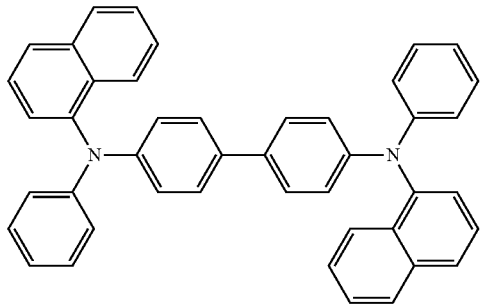

An organic EL device 200 manufactured in Example 1 and Comparative Example 1 is schematically illustrated in FIG. 2. The organic EL device 200 included an anode 201, a hole injection layer 203 on the anode 201, a hole transport layer 204 on the hole injection layer 203, a light-emitting layer 205 on the hole transport layer 204, a hole transport layer 206 and an electron injection layer 207 on the light-emitting layer 205, and a cathode 209 on the electron injection layer 207.

Performance characteristics of the organic EL device 200 of Example 1 and Comparative Example 1 are shown in Table 1.

TABLE 1

| | Hole transport material | Voltage (V) | Current efficiency (10 mA/cm$^2$) | Life span (hr) (1,000 cd/m$^2$) |
|---|---|---|---|---|
| Example 1 | Compound 2 | 7.5 | 6.5 | 2,000 |
| Comparative Example 1 | Comparative Compound 1 | 8.1 | 5.3 | 1,200 |

Electroluminescence characteristics of the manufactured organic EL device 200 were evaluated by using a brightness light distribution characteristics measurement system (Hamamatsu Photonics K.K., Model C9920-11).

As may be seen in Table 1, compared to the organic EL device of Comparative Example 1, the organic EL device of Example 1 exhibited higher luminous efficiency and 1.6 times greater life span.

The amine derivative according an embodiment may have a phenanthroimidazole group and may be capable of stably transporting holes with respect to electrons. Therefore, device degradation (which may be caused by electrons intruding into a hole transport layer) may be suppressed by using the amine derivative according to an embodiment, and high efficiency and long life span of the device may be realized.

While the above descriptions show and describe that an organic luminescence material according to an embodiment is used as a hole transport material of an organic EL device, the use of the organic luminescence material according to an embodiment is not limited to the organic EL device, and may be used for other light-emitting devices or apparatuses. Also, the organic EL device illustrated in FIGS. 1 and 2 may be applied to an active type organic EL device as well as a passive type organic EL device.

By way of summation and review, because of improvement in luminous characteristic and long life of an organic EL device, the hole transport layer may have excellent hole transport capability and carrier resistance. In this view, various hole transport materials have been considered.

The organic luminescence material according to an embodiment may be used as a hole transport material or the like.

The embodiments may provide organic EL devices of which life span is improved by suppressing device degradation that may be caused by electrons intruding into a hole transport layer.

According to an embodiment, an organic EL device having a long life span and improved luminous efficiency, and an organic luminescence material allowing the organic EL device to be realized and having improved electron resistance and luminous efficiency may be provided.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An amine derivative having a phenanthroimidazole group, the amine derivative being represented by Formula 1, below:

[Formula 1]

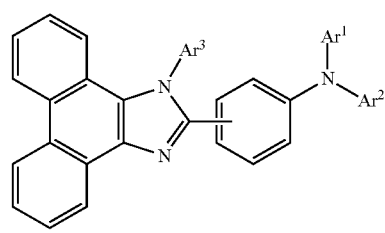

wherein:
Ar$^1$, Ar$^2$, and Ar$^3$ are each independently one of a substituent aryl group or a substituent heteroaryl group,
Ar$^1$, Ar$^2$, and Ar$^3$ are different substituents from one another, and
at least one of Ar$^1$, Ar$^2$, or Ar$^3$ has at least 12 carbon atoms.

2. The amine derivative as claimed in claim 1, wherein the amine derivative having the phenanthroimidazole group is represented by Formula 2, below:

[Formula 2]

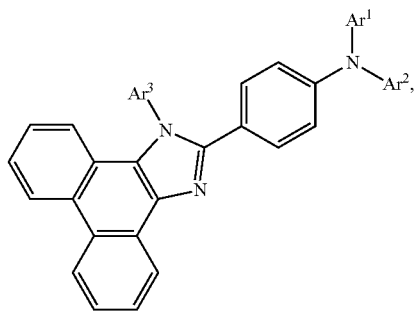

wherein $Ar^1$, $Ar^2$, and $Ar^3$ are as defined with respect to Formula 1.

3. The amine derivative as claimed in claim 1, wherein $Ar^1$, $Ar^2$, and $Ar^3$ are each independently one of a substituent dibenzoheterole group or a substituent aryl group having 6 to 18 carbon atoms.

4. The amine derivative as claimed in claim 1, wherein $Ar^1$, $Ar^2$, and $Ar^3$ are each independently one of a substituent dibenzofuran, a substituent dibenzothiophene, a substituent carbazole, a substituent fluorene, or a substituent phenyl.

5. An organic electroluminescence material comprising an amine derivative having a phenanthroimidazole group as claimed in claim 1.

6. An electroluminescence device, comprising:
an anode;
a cathode; and
a light-emitting layer and a hole transport layer between the cathode and the anode,
wherein the hole transport layer includes an amine derivative having the phenanthroimidazole group as claimed in claim 1.

7. An amine derivative having a phenanthroimidazole group, the amine derivative being represented by Formula 1, below:

[Formula 1]

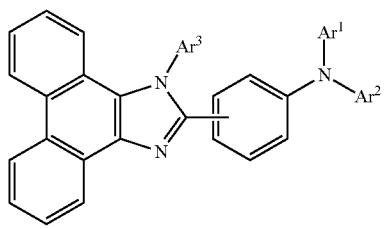

wherein:
$Ar^1$, $Ar^2$, and $Ar^3$ are each independently one of a substituent dibenzofuran, a substituent dibenzothiophene, a substituent carbazole, a substituent fluorene, or a substituent phenyl, and
at least one of $Ar^1$, $Ar^2$, or $Ar^3$ has at least 12 carbon atoms.

8. An organic electroluminescence material comprising an amine derivative having a phenanthroimidazole group as claimed in claim 7.

9. An electroluminescence device, comprising:
an anode;
a cathode; and
a light-emitting layer and a hole transport layer between the cathode and the anode,
wherein the hole transport layer includes an amine derivative having the phenanthroimidazole group as claimed in claim 7.

10. An amine derivative having a phenanthroimidazole group, the amine derivative including one of the following Compounds 1 to 28:

1

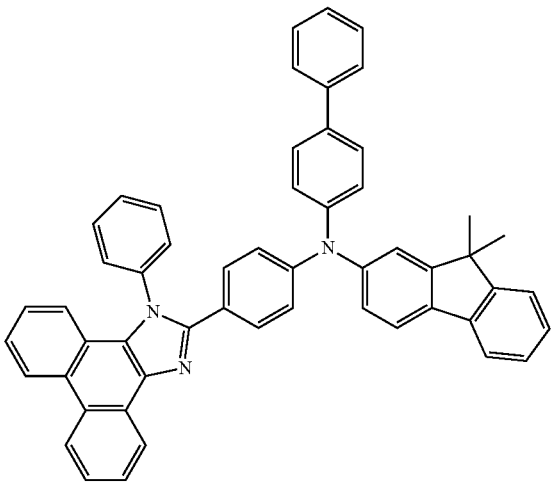

2

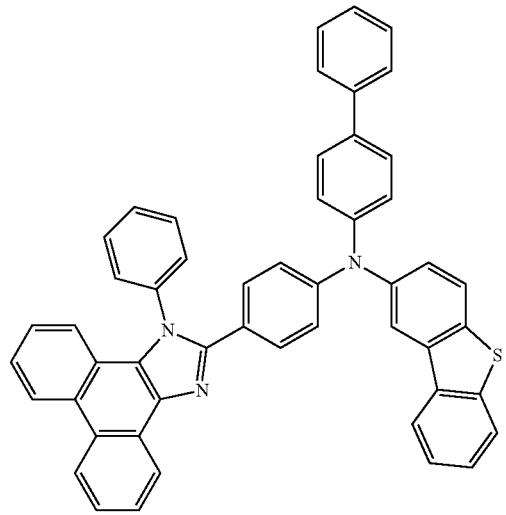

3

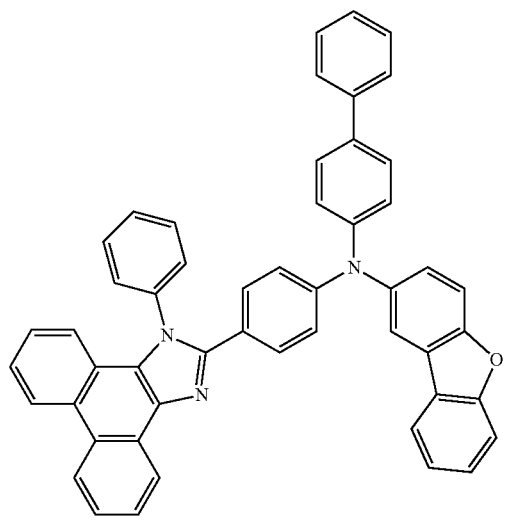

19
-continued
4
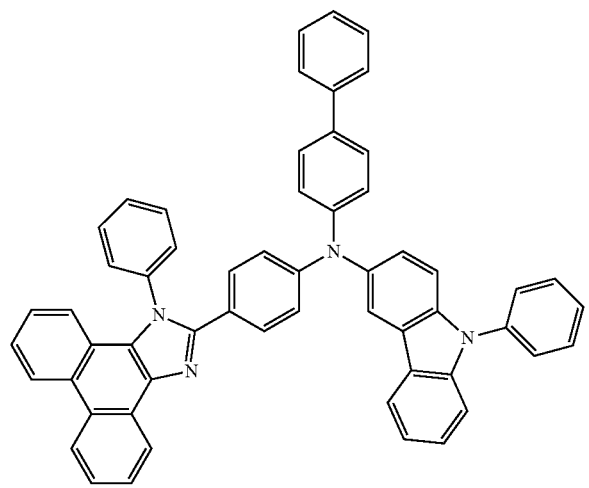
5
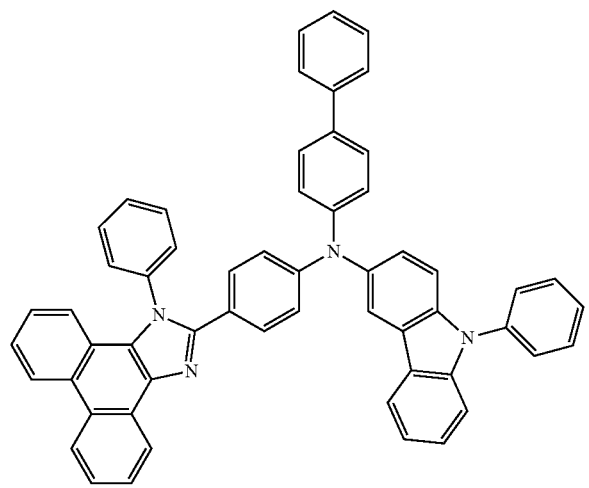
6
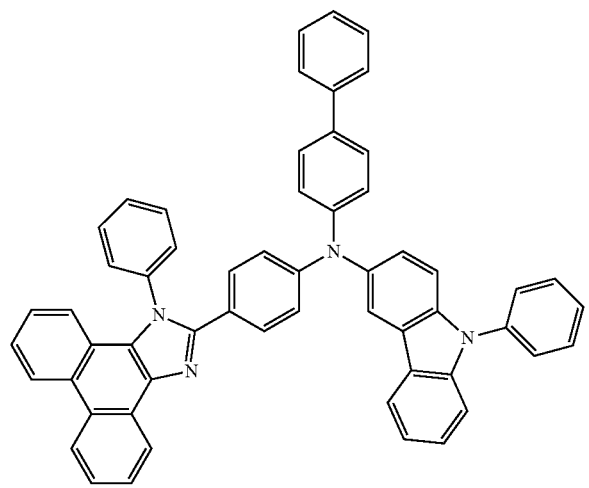
20
-continued
7
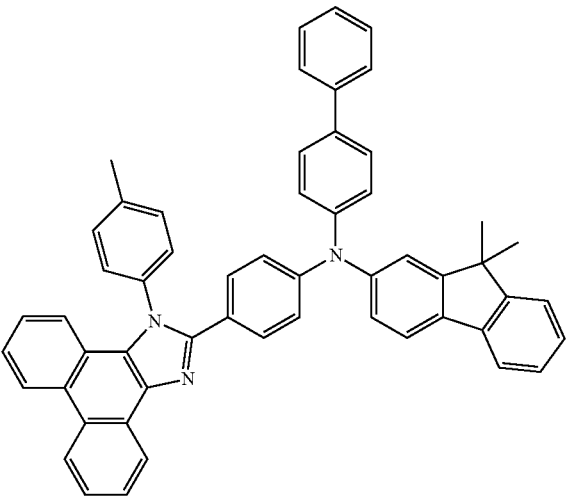
8
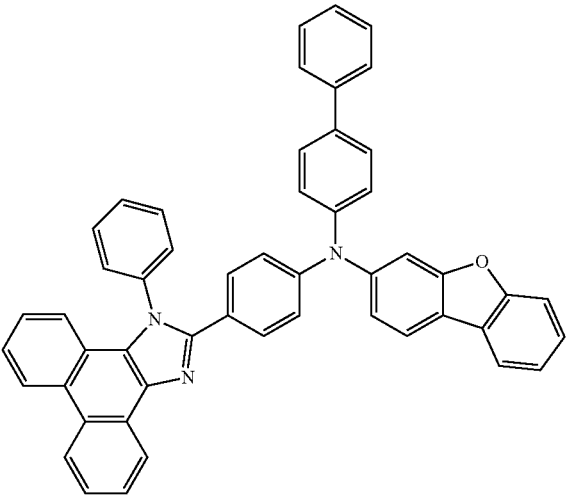
9
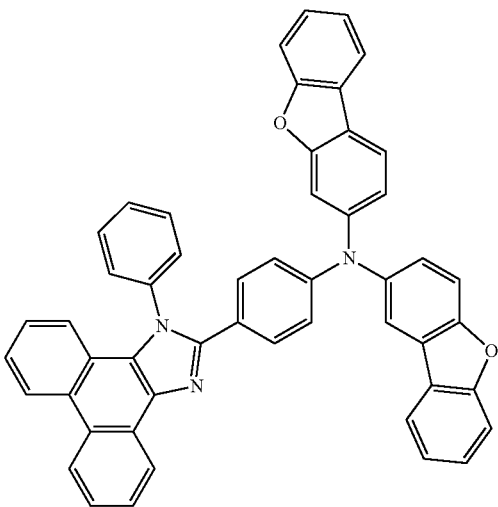

10
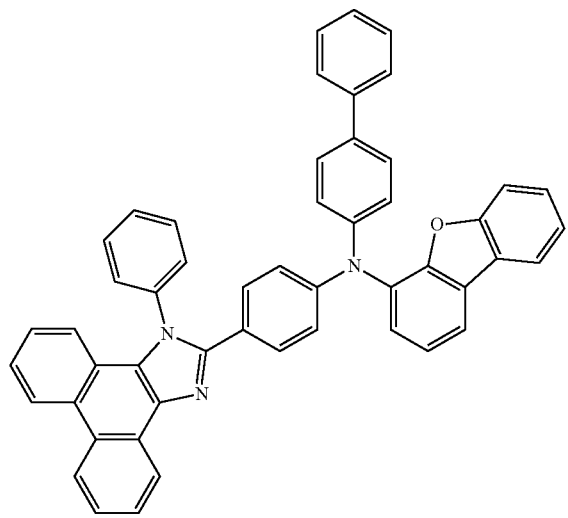
11
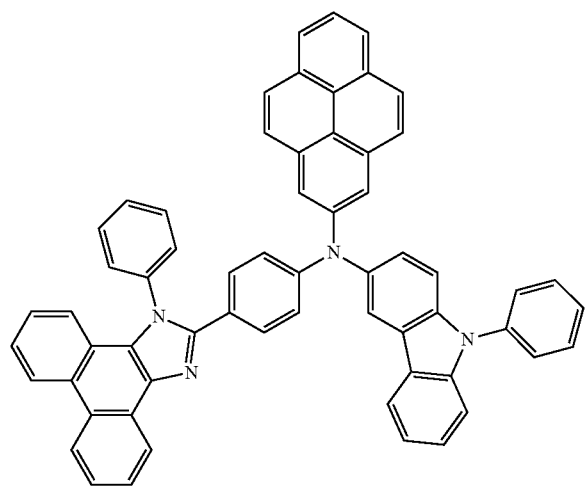
12
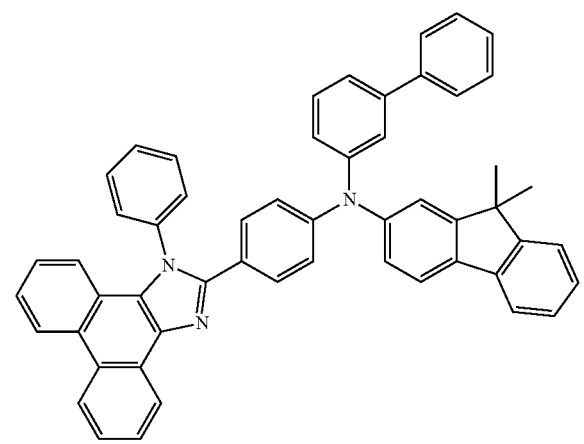
13
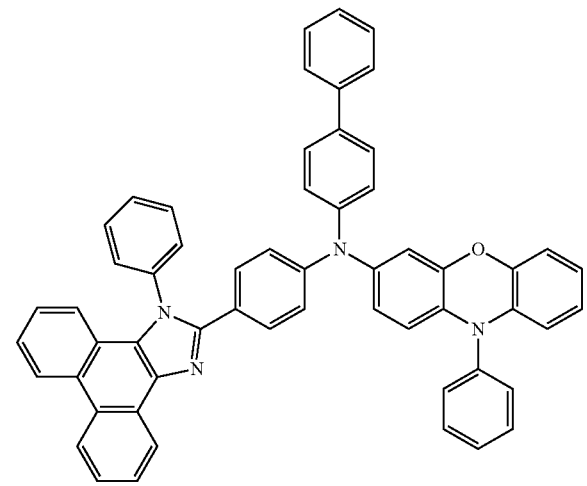
14
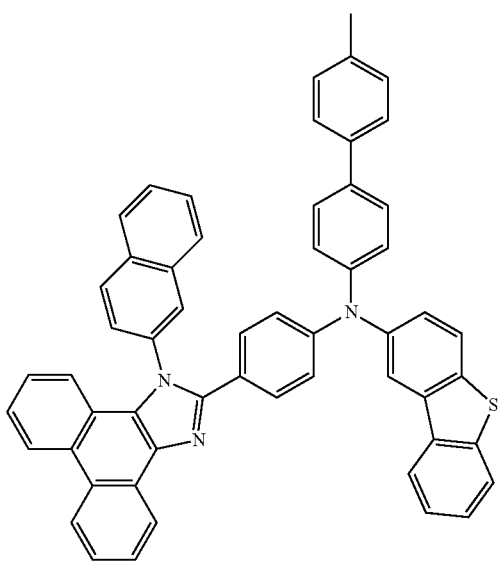
15
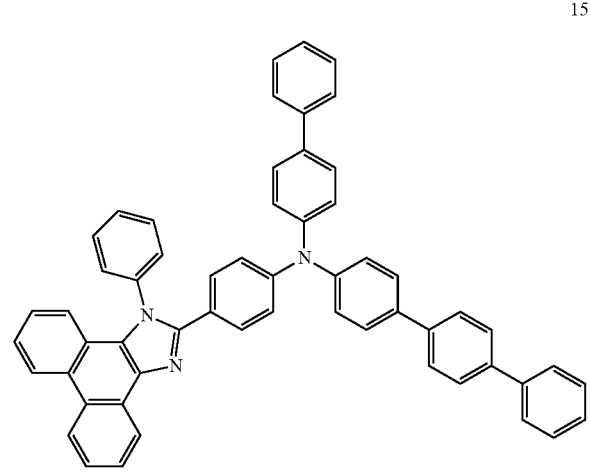

16
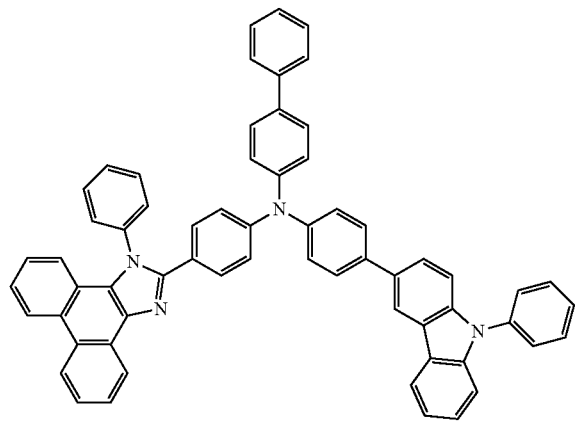
19
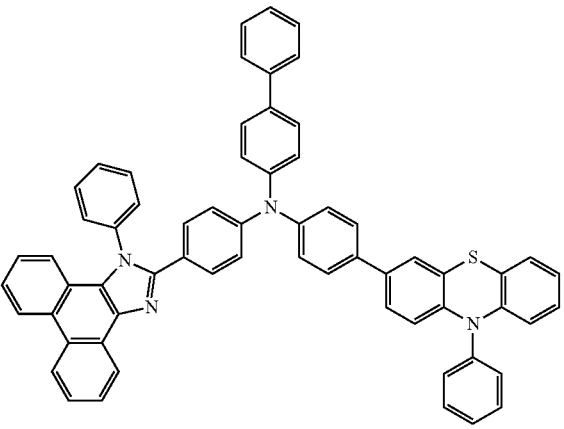
17
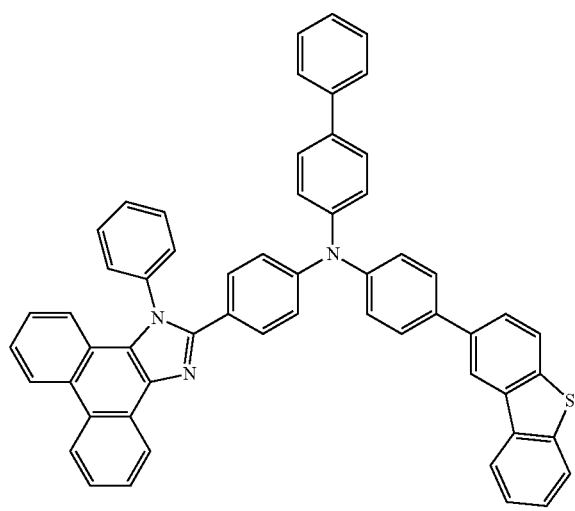
20
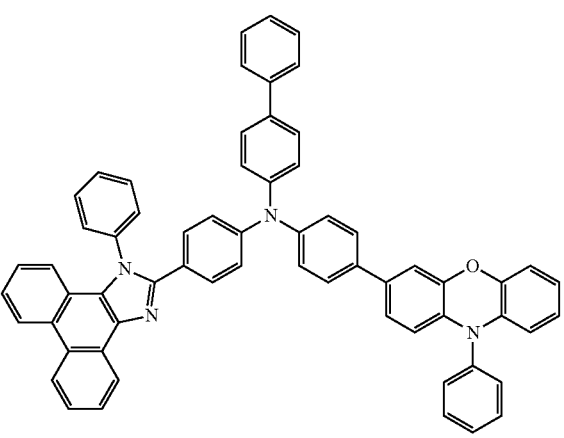
18
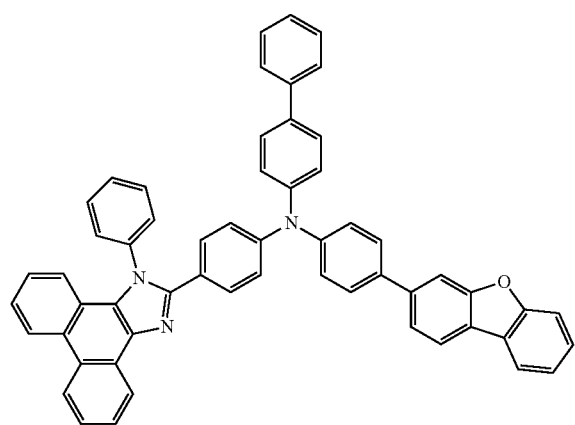
21
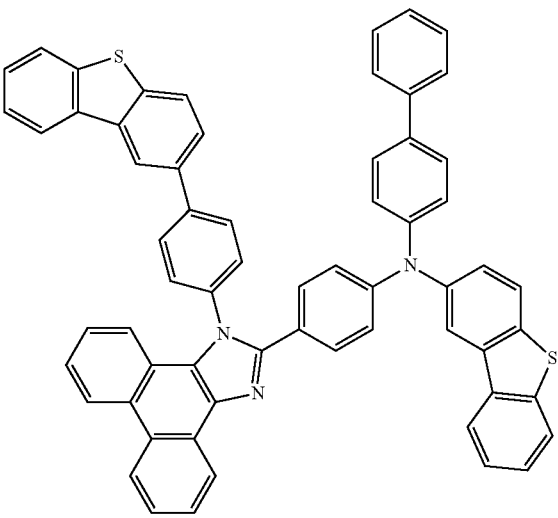

25
-continued
22
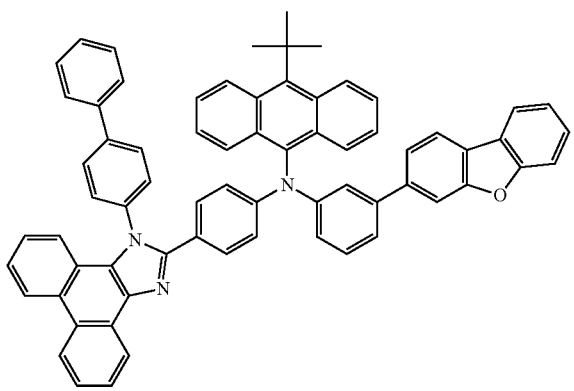
23
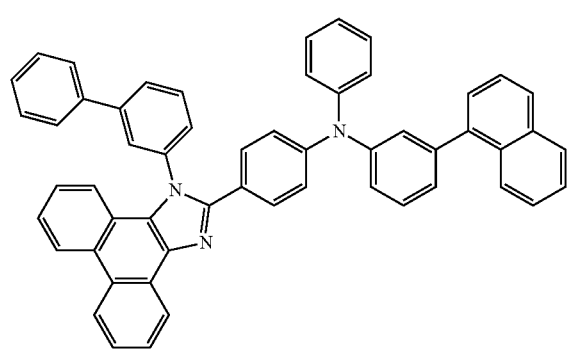
24
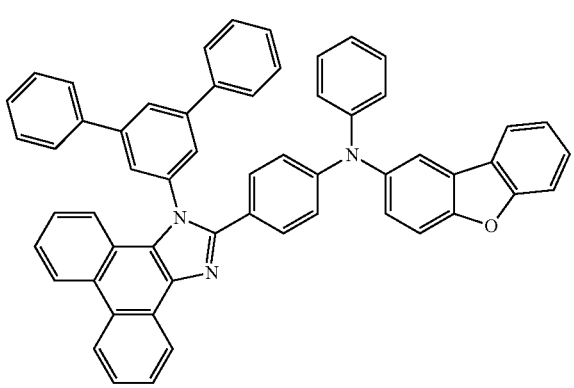
25
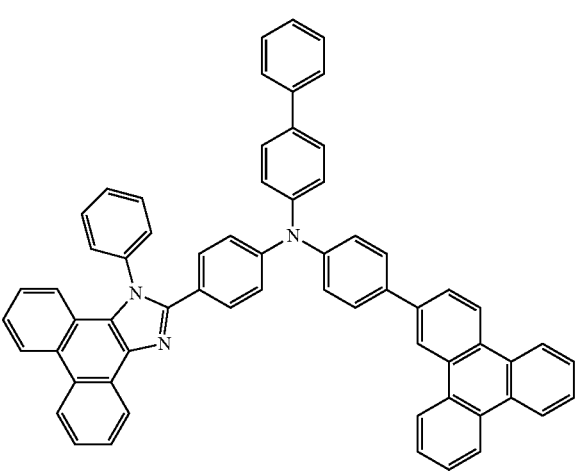
26
-continued
26
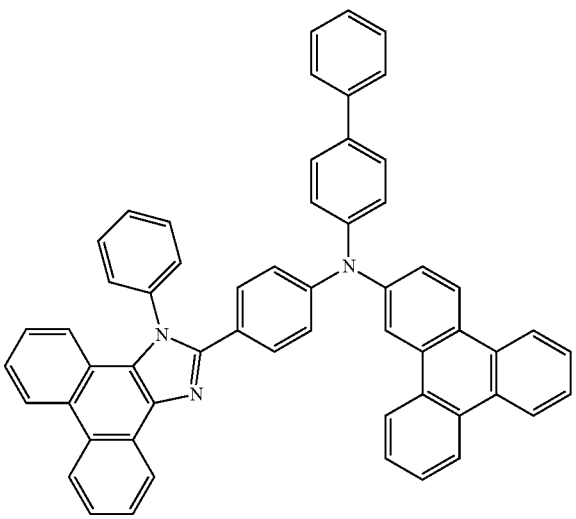
27
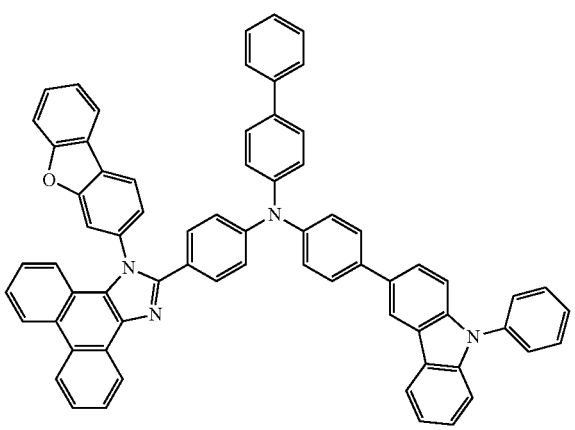
28
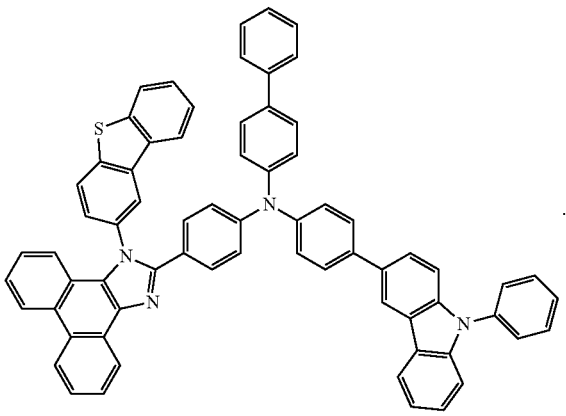
11. An organic electroluminescence material comprising an amine derivative having a phenanthroimidazole group as claimed in claim 10.
12. An electroluminescence device, comprising:
an anode;
a cathode; and
a light-emitting layer and a hole transport layer between the cathode and the anode, wherein the hole transport layer includes an amine derivative having the phenanthroimidazole group as claimed in claim 10.

\* \* \* \* \*